ization USDES010746832B2

(12) United States Patent
Huang et al.

(10) Patent No.: US 10,746,832 B2
(45) Date of Patent: Aug. 18, 2020

(54) DTI WITH CORRECTION OF MOTION-INDUCED DIFFUSION GRADIENT INCONSISTENCY

(71) Applicant: KONINKLIJKE PHILIPS N.V., Eindhoven (NL)

(72) Inventors: Feng Huang, Suzhou (CN); Zhigang Wu, Suzhou (CN); Zhongbiao Wu, Suzhou (CN)

(73) Assignee: Koninklijke Philips N.V., Eindhoven (NL)

( * ) Notice: Subject to any disclaimer, the term of this patent is extended or adjusted under 35 U.S.C. 154(b) by 13 days.

(21) Appl. No.: 16/064,665

(22) PCT Filed: Dec. 15, 2016

(86) PCT No.: PCT/EP2016/081088
§ 371 (c)(1),
(2) Date: Jun. 21, 2018

(87) PCT Pub. No.: WO2017/108543
PCT Pub. Date: Jun. 29, 2017

(65) Prior Publication Data
US 2018/0372829 A1    Dec. 27, 2018

(30) Foreign Application Priority Data

Dec. 22, 2015  (WO) ................ PCT/CN2015/098240
Apr. 26, 2016  (EP) .................................... 16166963

(51) Int. Cl.
*G01R 33/563* (2006.01)
*G01R 33/565* (2006.01)
(Continued)

(52) U.S. Cl.
CPC ........ *G01R 33/56341* (2013.01); *A61B 5/055* (2013.01); *G01R 33/5615* (2013.01); *G01R 33/56509* (2013.01); *G06T 7/20* (2013.01)

(58) Field of Classification Search
None
See application file for complete search history.

(56) References Cited

U.S. PATENT DOCUMENTS 5,833,609 A    11/1998  Daniels et al.
7,205,763 B2   4/2007   Porter
(Continued)

FOREIGN PATENT DOCUMENTS

WO        201491374 A2    6/2014

OTHER PUBLICATIONS

Jeong et al "High Resolution Human Diffusion Tensor Imaging Using 2-D Navigated Multishot Sense EPI at 7T" Magnetic Resonance in Medicine vol. 69, (3) NP. 793-802 (2013).
(Continued)

*Primary Examiner* — Douglas X Rodriguez

(57) ABSTRACT

A method and apparatus for magnetic resonance (MR) diffusion tensor imaging (DTI) with minimizes artifacts caused by motion-induced changes of the diffusion encoding. An object (10) is subject to at least one shot of a multi-echo imaging sequence to generate a train of echo signals. The multi-echo imaging sequence includes diffusion gradients, acquiring the echo signals for different diffusion gradients, detecting motion of the object (10) during acquisition of the echo signals, determining a plurality of motional states of the object (10) based on the detected motion, wherein the object (10) is stationary in each detected motional state, determining directions of the diffusion gradients relative to a reference frame of the object (10) for detected motional states of the object (10), respectively, and
(Continued)

deriving diffusion coefficients from the acquired echo signals for the determined relative directions of the diffusion gradients.

12 Claims, 2 Drawing Sheets

(51) Int. Cl.
    *A61B 5/055*         (2006.01)
    *G01R 33/561*      (2006.01)
    *G06T 7/20*          (2017.01)

(56) References Cited

U.S. PATENT DOCUMENTS

| | | | |
|---|---|---|---|
| 2005/0237057 A1* | 10/2005 | Porter | G01R 33/56341 324/307 |
| 2009/0284257 A1* | 11/2009 | Bammer | G01R 33/56341 324/307 |
| 2012/0259199 A1 | 10/2012 | Huwer et al. | |
| 2014/0002078 A1 | 1/2014 | Chen et al. | |

OTHER PUBLICATIONS

M. Aksoy "Effects of Motion and B-Matrix Correction for High Resolution DTI With Short Axis Propeller-EPI" NMR in Biomedicine, vol. 23, No. 7, Mar. 11, 2010.

M. Aksoy "Single Step Nonlinear Diffusion Tensor Estimation in the Presence of Microscopic and Macroscopic Motion" Magnetic Resonance in Medicine, vol. 59, No. 5, Apr. 21, 2008 p. 1138-1150.

M.-L. Chu, et al., "Correction of 3D motion induced artifacts in multi-shot diffusion imaging using projection onto convex sets based multiplexed sensitivity-encoding MRI (POCSMUSE)," in ISMRM 2015 Annual Meeting, Toronto, Canada, 2015, p. 960.

N.-k. Chen, et al., "A robust multi-shot scan strategy for high-resolution diffusion weighted MRI enabled by multiplexed sensitivity-encoding (MUSE)," NeuroImage, vol. 72, pp. 41-47, 2013.

Barbara A.K. Kreilkamp et al "Retrospective Head Motion Correction Approaches for Diffusion Tensor Imaging:Effects of Preprocessing Choices on Biases and Reproducibility of Scalar Diffusion Metrics" Magn Reson Imaging. Jan. 2016;43(1):99-106. doi: 10.1002/jmri.24965. Epub Jun. 7, 2015.

Theodore P. Trouard et al Analysis and Comparison of Motion-Correction Techniques in Diffusion-Weighted Imaging; 2nd Annual Meeting of the Society of Magnetic Resonance 1994, San Francisco, CA.

Adam W. Anderson et al "Analysis and Correction of Motion Artifacts in Diffusion Weighted Imaging" Magn Reson Med. Sep. 1994;32(3):379-87.

Shayan Guhaniyogi et al: "Motion immune diffusion imaging using augmented MUSE for high-resolution multi-shot EPI",Magnetic Resonance in Medicine., vol. 75, No. 2, Mar. 11, 2015 (Mar. 11, 2015),pp. 639-652.

G.K. Rohde et al: "Comprehensive approach for correction of motion and distortion in diffusion-weighted MRI", Magnetic Resonance in Medicine, vol. 51, No. 1, Jan. 1, 2003 (Jan. 1, 2003), pp. 103-114.

Samantha J. Holdsworth et al: "Diffusion tensor imaging (DTI) with retrospective motion correction for large-scale pediatric imaging",Journal of Magnetic Resonance Imaging, vol. 36, No. 4, Jun. 11, 2012 (Jun. 11, 2012), pp. 961-971, XP055185496,ISSN: 1053-1807, DOI: 10.1002/jmri.23710 p. 962-p. 966.

Jessica Dubois et al; "Correction strategy for diffusion-weighted images corrupted with motion: application to the DTI evaluation of infants' white matter",Magnetic Resonance Imaging,vol. 32, No. 8, Jun. 21, 2014 (Jun. 21, 2014), pp. 981-992.

A. Alhamud et al: "Volumetric navigators for real-time motion correction in diffusion tensor imaging", Magnetic Resonance in Medicine, vol. 68, No. 4,Jan. 13, 2012 (Jan. 13, 2012), pp. 1097-1108.

Murat Aksoy et al: "Real-time optical motion correction for diffusion tensor imaging", Magnetic Resonance in Medicine, vol. 66, No. 2, Mar. 22, 2011 (Mar. 22, 2011),pp. 366-378.

Chen Nan-Kuei et al: "A robust multi-shot scan strategy for high-resolution diffusion weighted MRI enabled by multiplexed sensitivity-encoding (MUSE)", Neuroimage, Elsevier, Amsterdam, NL, vol. 72, Jan. 28, 2013 (Jan. 28, 2013), pp. 41-47.

Ha-Kyu Jeong et al: "High-resolution human diffusion tensor imaging using 2-D navigated multishot Sense EPI at 7 T", Magnetic Resonance in Medicine., vol. 69, No. 3, May 16, 2012 (May 16, 2012), pp. 793-802.

* cited by examiner

DTI WITH CORRECTION OF MOTION-INDUCED DIFFUSION GRADIENT INCONSISTENCY

CROSS REFERENCE TO RELATED APPLICATIONS

This application is a U.S. national phase application of International Application No. PCT/EP2016/081088, filed on Dec. 15, 2016, which claims the benefit of PCT/CN2015/098240 filed Dec. 22, 2015 and EP application 16166963.5 filed Apr. 26, 2016, both of which are incorporated herein by reference.

FIELD OF THE INVENTION

The invention relates to the field of magnetic resonance (MR) imaging. It concerns a method of MR imaging of an object. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for imaging of soft tissue they are superior to other imaging methods in many respects, do not require ionizing radiation and are usually not invasive.

According to the MR method in general, the object, for example the body of the patient to be examined, is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse), so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

To realize spatial resolution in the body, constant magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to a MR image by means of an image reconstruction algorithm.

MR imaging is sensitive to diffusion. Known diffusion weighted imaging (DWI) techniques are commonly performed by using imaging sequences comprising diffusion gradients, wherein the diffusion of protons (of water molecules) along the direction of the diffusion gradient reduces the amplitude of the acquired MR signals. Diffusion tensor imaging (DTI) is a more sophisticated form of DWI, which allows for the determination of both the magnitude and the directionality of diffusion. For example, DTI enables to visualize white matter fibers in MR brain imaging and can map subtle changes in the white matter associated with diseases like brain infarction, multiple sclerosis, epilepsy etc. The so-called fractional anisotropy (FA) provides information about the shape of the diffusion tensor at each voxel position of a MR image. The FA is determined from the variance of the eigenvalues of the diffusion tensor. Hence, the FA reflects differences between the isotropic and the linear diffusion at a given image position. A technique called diffusion tensor tractography (DTT) has been developed recently as a variant of DTI. This technique enables the non-invasive tracking of neuronal fibers in the brain. White matter fiber trajectories are reconstructed by tracking the direction of fastest diffusion which is assumed to correspond to the longitudinal axis of the fiber.

Brain DWI techniques are particularly vulnerable to macroscopic head motion, as the signal attenuation resulting from the motion can confound the measurement of interest. Subject motion during an MR examination can be particularly problematic in populations like children, the elderly, or patients with medical conditions that prevent them from lying still, such as Parkinson's disease. Motion affects the data in two main ways: shifts of the brain tissue to be imaged (resulting in ghosting artifacts in the reconstructed MR images), and exposure to incorrect diffusion encoding.

Retrospective motion correction methods prior to determining the diffusion tensor are widely used. A basic and common way of retrospectively correcting for motion time employs a co-registration of the diffusion-weighted MR image to a reference (unweighted) MR image and a subsequent reorientation of the diffusion gradient directions that takes into account the motion at each image position. Such operations involve spatial interpolations, and these can affect partial volume effects, the variance properties of the DWI with propagation in the diffusion tensor calculation.

To avoid significant artifacts resulting from motion, DWI data have commonly been acquired using single-shot imaging sequences, such as single-shot echo-planar imaging (EPI). However, the image quality can be low and the spatial resolution is limited in single-shot DWI. The significant geometric distortions and limited spatial resolution make it difficult to measure diffusion properties at high precision. Recent efforts have been made to address the limitations of single-shot DWI.

US 2014/0002078 A1 describes a multi-shot DWI technique (termed multiplexed sensitivity encoding—MUSE) which uses parallel acquisition and inherently corrects shot-to-shot phase variations due to motion and thus avoids ghosting artifacts. Jeong et al. (Magnetic Resonance in Medicine, volume 69 (3), pages 793-802, 2013) propose a multi-shot DWI technique using a modification of the standard SENSE algorithm commonly used for fast parallel image acquisition. The modification accounts for shot-to-shot motion-induced phase errors. This known technique is termed image reconstruction using image-space sampling functions (IRIS).

However, these techniques do not take the motion-induced incorrect diffusion encoding into account.

"Effects of motion and b-matrix correction for high resolution DTI with short-axis PROPELLER-EPI" by MURAT AKSOY proposes diffusion tensor estimated directly from the complex k space data, by solving the equation with rotation and translation matrices R and Ar from the scanner frame of reference to the patient frame of reference. The equation is solved using non-linear conjugate gradient algorithm, which is described in details in "Single-step nonlinear diffusion tensor estimation in the presence of microscopic and macroscopic motion".

SUMMARY OF THE INVENTION

From the foregoing it is readily appreciated that there is a need for an improved DWI technique. It is consequently an object of the invention to enable DWI (and DTI/DTT) with minimization of artifacts caused by motion-induced changes of the diffusion encoding.

In accordance with the invention, a method of MR imaging of an object placed in an examination volume of a MR device is disclosed. The method comprises the steps of:
  subjecting the object to at least one shot of a multi-echo imaging sequence, a train of echo signals being generated by the shot, wherein the multi-echo imaging sequence comprises diffusion gradients;
  acquiring the echo signals for different diffusion gradients;
  detecting motion of the object (10) during acquisition of the echo signals;
  determining a plurality of motional states of the object (10) based on the detected motion, wherein the object (10) is stationary in each detected motional state;
  determining directions of the diffusion gradients relative to a reference frame of the object (10) for detected motional states of the object (10), respectively; and
  deriving diffusion coefficients from the acquired echo signals for the determined relative directions of the diffusion gradients.

In other words, the invention proposes to treat the motion-induced changes in the relative directions of the diffusion gradient as additional diffusion gradient directions and to directly use these in the calculation of the diffusion coefficients.

A reference frame within the meaning of the invention is, for example, a coordinate system which is in a fixed spatial relation to the examined object, such as, for example, the head of a patient.

It is assumed in the technique of the invention that no object motion and thus no variations of the diffusion gradient directions in the reference frame of the object occur while the object is in one particular motional state. If motion is detected, the position and orientation of the imaged object changes. Detected motion thus temporally separates one motional state from the other within the meaning of the invention. The acquired echo signals are attributed to the different motional states. Each diffusion coefficient is computed according to the invention from the echo signals and the determined diffusion gradient directions that are attributed to the same motional state such that, finally, a diffusion tensor is obtained in the reference frame of the object.

With this approach it is not necessary to correct for variations of the diffusion encoding prior to calculating the elements of the diffusion tensor.

Preferably, an image is produced from the diffusion coefficients obtained in accordance with the invention. The image may be a fractional anisotropy (FA) map, a mean diffusivity (MD) map, a radial diffusivity (RD) map or an axial diffusivity (AD) map, as commonly used in clinical studies, or a map of any other scalar metric derived from the diffusion coefficients.

One 'shot' of the multi-echo imaging sequence according to the invention comprises an initial RF pulse for excitation of magnetic resonance followed by at least one (typically 180°) refocusing RF pulses, wherein diffusion gradients are applied prior to and after the refocusing RF pulse. This sequence of pulses generates a diffusion-encoded spin echo which is measured as a train of differently phase- and frequency-encoded gradient-recalled echo signals. These echo signals are acquired, wherein each echo signal represents a k-space profile. One single shot or a plurality of shots of the multi-echo sequence may be applied for completely sampling k-space in order to be able to reconstruct a full MR image from the acquired signal data. A multi-shot multi-echo imaging sequence may be preferred to achieve high image quality and to measure diffusion properties at high precision.

In an embodiment of the invention, motion may be detected only between different shots of the multi-echo imaging sequence. It is assumed in this case that no motion occurs during each shot of the sequence such that each shot can be attributed to one motional state of the object (multiple shots may be attributed to the same motional state). If k-space is sampled completely in a single shot or a group of shots of the sequence it is possible to reconstruct a full image from the echo data acquired in this shot/group of shots and to compute the diffusion coefficients for the relative gradient directions attributed to this shot/group of shots. The remaining tensor elements of the diffusion tensor may then be calculated from the echo signal data and the relative gradient directions attributed to other shots of the imaging sequence.

Similarly, the echo signals may be acquired using signal averaging for improving the signal-to-noise ratio (SNR). In this case, motion between different signal averaging steps may detected and each signal averaging step is then attributed to one motional state of the object. A MR image is reconstructed from the echo data acquired in one signal averaging step and the diffusion coefficients are calculated for the relative gradient directions attributed to this averaging step. The remaining tensor elements of the diffusion tensor may then be calculated from the echo signal data and the relative gradient directions attributed to other signal averaging steps of the imaging sequence.

For DTI it is necessary to acquire signal data for a set of two or more different diffusion gradient directions and to calculate diffusion coefficients for each of the different diffusion gradient directions. The gradient direction is varied in a number of consecutive steps. Motion may be detected between variations of the diffusion gradient directions such that each diffusion gradient direction is then attributed to one motional state of the object. A MR image is reconstructed from the echo data acquired for each diffusion gradient direction and the diffusion coefficients are calculated for the corresponding gradient directions in the reference frame of the object. The remaining tensor elements of the diffusion tensor may then be calculated from the echo signal data and the relative gradient directions attributed to other diffusion gradient variation steps.

In one possible embodiment, the imaging sequence used in the method of the invention is a multi-shot EPI sequence.

Motion may be detected, for example, by the known navigator technique. For this purpose, the generation of navigator echoes may be incorporated into the imaging sequence used according to the invention. Alternatively, motion may be detected by the use of k-space consistency criteria, by registration of low-resolution MR images reconstructed from a part of the acquired echo signal data, or by internal and/or external motion sensors. If motion is detected, the changed orientation of the diffusion gradient relative to the reference frame of the object is determined and attributed to the new motional state of the object.

The method of the invention described thus far can be carried out by means of a MR device including at least one main magnet coil for generating a uniform static magnetic field within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit. The method of the invention can be implemented, for example, by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
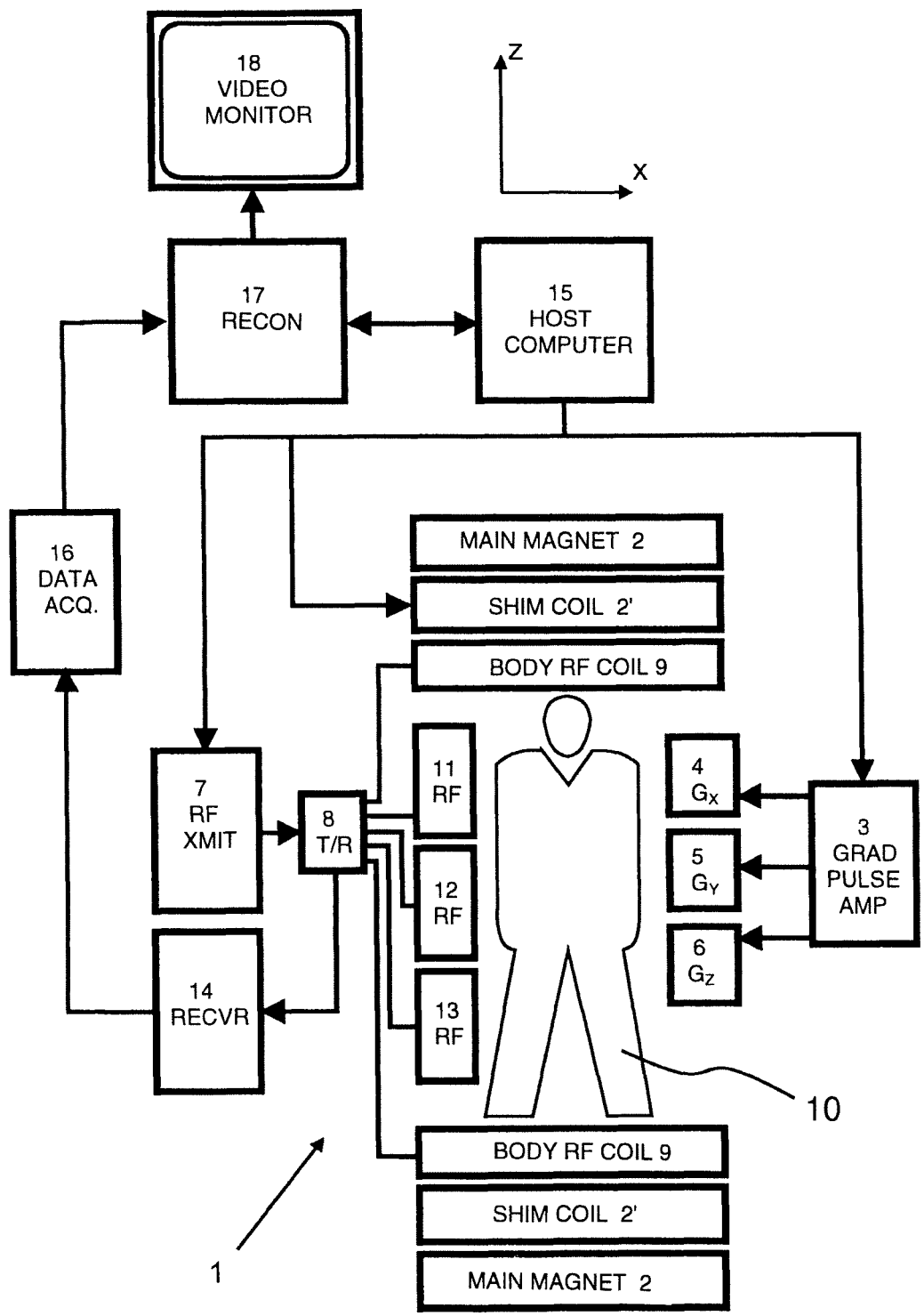
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10, a set of local array RF coils 11, 12, 13 are placed contiguous to the region selected for imaging. The array coils 11, 12, 13 can be used to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as diffusion weighted echo planar imaging (DW-EPI) or the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such as SENSE, SMASH, or GRAPPA. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

With continuing reference to FIG. 1 and with further reference to FIGS. 2 and 3 embodiments of the method of the invention are explained in the following.

Figure 2:
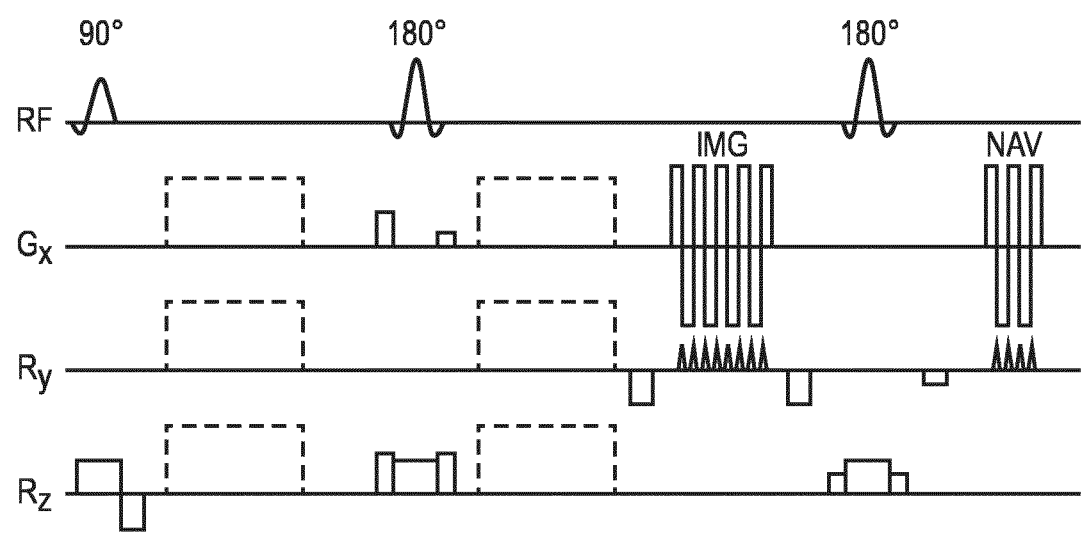
FIG. 2 *shows* a diagram of an imaging sequence used in an embodiment of the invention.

The body 10 is subjected to multiple shots of a multi-echo imaging sequence as illustrated in FIG. 2. The imaging sequence is a spin echo diffusion weighted multi-shot EPI sequence. The second 180° RF refocusing pulse is followed by a navigator echo acquisition NAV. The echo signal acquisition IMG used for the actual diffusion imaging as well as the navigator echo acquisition NAV may be accelerated by SENSE. Different diffusion gradient directions are applied using multiple shots of the imaging sequence. The dotted lines in FIG. 2 represent the diffusion gradients applied before and after the first 180° RF refocusing pulse. Echo signals are acquired for different diffusion gradients.

Motion of the object is detected using the navigator echoes. Diffusion gradient directions relative to the body 10 are determined from the detected motion, meaning that the directions of the diffusion gradients are determined relative to the reference frame of the body 10 for each detected motional state of the body 10. A set of thus determined relative gradient directions is attributed to each motional state of the body 10.

For example, echo signals are acquired using the imaging sequence shown in FIG. 2 for three different directions of the diffusion gradient. A full k-space echo signal data set is acquired in four shots of the imaging sequence. Three signal averaging steps are used (number of signal averages NSA=3). This means that 3×4×3=36 shots are performed. Each group of 12 shots shares the same diffusion gradient direction. Motion is detected resulting in the identification of, for example, five different motional states of the body 10. The directions of the diffusion gradients relative to the reference frame of the body 10 are determined for each motional state from the navigator echoes. These five relative gradient directions are attributed, in the example, to groups of 8, 10, 4, 6, 8 shots of the imaging sequence respectively. No motion occurs during the acquisition of each of these five groups. The above mentioned IRIS or MUSE techniques may be used for the reconstruction of an image for each group of shots, thereby correcting for motion-induced phase inconsistencies. These five images are then registered in image space and diffusion coefficients for the five relative gradient directions are derived.

Figure 3:
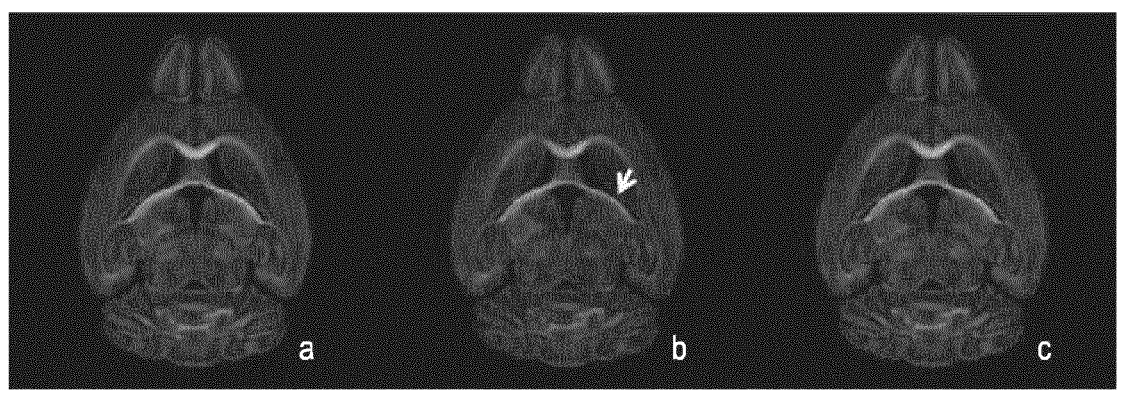
FIG. 3 shows FA maps derived with and without the gradient inconsistency compensation of the invention.

FIG. 3 shows FA maps derived with and without the diffusion gradient inconsistency compensation of the invention. FIG. 3a shows the FA map without any motion. In FIGS. 3b and 3c, a rotation of the imaged head by 40° occurred during acquisition. FIG. 3b shows the FA map derived only with phase and magnitude inconsistency correction (using the MUSE or IRIS scheme). FIG. 3c shows the FA map derived with phase and magnitude inconsistency correction (MUSE/IRIS) as well as gradient direction consideration according to the invention. The white arrow in FIG. 3b shows the location of an artifact that is due to motion-induced inconsistent diffusion encoding. This artifact is not visible in FIG. 3c.

To further demonstrate the effect of the invention, two regions of interest are selected in the image data of FIG. 3 in the genu and splenium of the corpus callosum (GCC and SCC) respectively. The following table shows the angular deviation (AD) of the major eigenvector of the diffusion tensor in degrees determined without using the method of the invention (by comparing the data on which FIGS. 3a and 3b are based) and with using the method of the invention (by comparing the data on which FIGS. 3a and 3c are based), and, in the same manner, the root mean square error (RMSE) of the FA.

|  | AD (SCC) | AD (GCC) | RMSE (SCC) | RMSE (GCC) |
| --- | --- | --- | --- | --- |
| Without invention | 18 +− 20 | 17 +− 7 | 28% | 22% |
| With invention | 4.5 +− 2 | 8 +− 3.6 | 10.7% | 9.4% |

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of magnetic resonance (MR) imaging of an object placed in an examination volume of a MR device, the method comprising:
   subjecting the object to at least one shot of a multi-echo imaging sequence, a train of echo signals being generated by the shot, wherein the multi-echo imaging sequence comprises diffusion gradients;
   acquiring the echo signals for diffusion gradients with different applied directions;
   detecting motion of the object during acquisition of the echo signals;
   from the detected motion, determining a plurality of different motion states in which the object is stationary;
   attributing the acquired echo signals to the different motion states;
   determining directions of the diffusion gradients relative to a reference frame of the object for the different detected motion states of the object, respectively; and
   deriving diffusion coefficients from the acquired echo signals for the different determined relative directions of the diffusion gradients by computing each diffusion coefficient according to the echo signals and each determined diffusion gradient direction that are attributed to the same motion state.

2. The of claim 1, wherein the object is subjected to a number of shots of the multi-echo imaging sequence.

3. The method of claim 1, wherein the multi-echo imaging sequence comprises navigator echoes.

4. The method of claim 3, wherein the motion is detected using the navigator echoes.

5. The method of claim 1, wherein the echo signals are acquired using signal averaging.

6. The method of claim 5, wherein motion between different signal averaging steps is detected and each signal averaging step is attributed to one of the determined motion states of the object.

7. The method of claim 1, wherein the imaging sequence is a multi-shot EPI sequence.

8. The method of claim 1, further comprising:
   correcting the reconstructed images for motion-induced phase inconsistencies.

9. A method of magnetic resonance (MR) imaging of an object placed in an examination volume of a MR device, the method comprising:
   subjecting the object to at least one shot of a multi-echo imaging sequence to generate a train of echo signals, wherein the multi-echo imaging sequence includes diffusion gradients and navigation echoes;
   acquiring the echo signals for diffusion gradients with different applied directions;
   detecting motion of the object during acquisition of the echo signals;
   from the detected motion, determining a plurality of different motion states in which the object is stationary;
   determining directions of the diffusion gradients relative to the reference frame of the object for each of the plurality of motion states of the object from the navigator echoes.

10. The method of claim 9, further comprising:
attributing the acquired echo signals to the different motion states; and
computing each diffusion coefficient according to the echo signals and each determined diffusion gradient direction that are attributed to the same motion state.

11. A magnetic resonance (MR) device including at least one main magnet coil configured to generate a static magnetic field within an examination volume;
a plurality of gradient coils configured to generate magnetic field gradients in different spatial directions within the examination volume;
at least one RF coil configured to generate RF pulses within the examination volume and/or to receive MR signals from an object positioned in the examination volume;
one or more computer processors configured to:
control the gradient coils and the at least one RF coil to subject the object to at least one shot of a multi-echo imaging sequence, the multi-echo imaging sequence applying diffusion gradients in a plurality of different preselected diffusion gradient directions to generate a train of echo signals with the plurality of different preselected diffusion gradient directions;
acquire the train of echo signals;
detect motion of the object during acquisition of the echo signals;
determine a plurality of motion states of the object based on the detected motion, wherein the object is stationary during each of the detected motion states;
determine directions of the diffusion gradients relative to a reference frame of the object for detected motion states of the object; and
calculate diffusion coefficients from the acquired echo signals for the determined relative directions of the diffusion gradients by treating motion-induced changes in the relative directions of the diffusion gradient as additional applied directions, without correcting for variations in diffusion encoding prior to calculating the diffusion coefficients.

12. A non-transitory computer-readable medium carrying a computer program configured to be run on a magnetic resonance (MR) device, which computer program comprises instructions for:
generating a multi-echo imaging sequence, the multi-echo imaging sequence applying diffusion gradients in a plurality of preselected diffusion gradient directions to induce a train of echo signals;
acquiring the train of echo signals induced by the multi-echo imaging sequence;
detecting motion of the object during acquisition of the echo signals;
determining a plurality of motion states of the object based on the detected motion, wherein the object is stationary in each detected motion state;
determining directions of the diffusion gradients relative to a reference frame of the object for each of the detected motion states of the object; and
calculate diffusion coefficients directly from the acquired echo signals for the determined relative directions of the diffusion gradients for each of the motion states, such that the motion-induced changes in the relative directions of the diffusion gradient are treated as diffusion gradient directions without correcting for motion-induced variations in diffusion encoding prior to calculating the diffusion coefficients.

* * * * *